(12) United States Patent
Zugates et al.

(10) Patent No.: US 9,623,143 B2
(45) Date of Patent: Apr. 18, 2017

(54) FOAM-BASED MEDICAL TREATMENTS

(71) Applicants: Gregory T. Zugates, Chelmsford, MA (US); Adam Rago, Falmouth, MA (US); Toby Freyman, Lexington, MA (US); Upma Sharma, Somerville, MA (US); Rany Busold, Medford, MA (US); John Caulkins, Watertown, MA (US); Parisa Zamiri, Brookline, MA (US); Jennifer Mortensen, Somerville, MA (US); Meghan McGill, Northborough, MA (US); Daniel K. Bonner, Somerville, MA (US)

(72) Inventors: Gregory T. Zugates, Chelmsford, MA (US); Adam Rago, Falmouth, MA (US); Toby Freyman, Lexington, MA (US); Upma Sharma, Somerville, MA (US); Rany Busold, Medford, MA (US); John Caulkins, Watertown, MA (US); Parisa Zamiri, Brookline, MA (US); Jennifer Mortensen, Somerville, MA (US); Meghan McGill, Northborough, MA (US); Daniel K. Bonner, Somerville, MA (US)

(73) Assignee: ARSENAL MEDICAL, INC., Watertown, MA (US)

( * ) Notice: Subject to any disclaimer, the term of this patent is extended or adjusted under 35 U.S.C. 154(b) by 437 days.

(21) Appl. No.: 14/215,988

(22) Filed: Mar. 17, 2014

(65) Prior Publication Data
US 2014/0316367 A1 Oct. 23, 2014

Related U.S. Application Data

(63) Continuation-in-part of application No. 13/536,557, filed on Jun. 28, 2012.
(Continued)

(51) Int. Cl.
*A61M 35/00* (2006.01)
*A61F 13/15* (2006.01)
(Continued)

(52) U.S. Cl.
CPC ....... *A61L 24/0015* (2013.01); *A61L 24/0036* (2013.01); *A61L 24/046* (2013.01); *A61L 2300/418* (2013.01); *A61L 2400/04* (2013.01)

(58) Field of Classification Search
CPC ........... A61L 2300/418; A61L 2400/04; A61L 24/0015; A61L 24/0036; A61L 24/046
See application file for complete search history.

(56) References Cited

U.S. PATENT DOCUMENTS

| | | | | | |
|---|---|---|---|---|---|
| 3,937,223 | A | * | 2/1976 | Roth | A61L 15/64 602/45 |
| 2006/0173492 | A1 | * | 8/2006 | Akerfeldt | A61B 17/0057 606/232 |

(Continued)

*Primary Examiner* — Rebecca E Eisenberg

(57) ABSTRACT

The present invention relates generally to systems and methods and systems for generating polymer foams within body cavities to locate and/or control bleeding. The present invention further relates to methods and systems for generating polymer foams within non-compressible wounds to control or stop bleeding. The present invention further relates to the use of foams and gels for medical and cosmetic purposes.

21 Claims, 12 Drawing Sheets

Related U.S. Application Data

(60) Provisional application No. 61/554,181, filed on Nov. 1, 2011, provisional application No. 61/852,053, filed on Mar. 15, 2013, provisional application No. 61/852,225, filed on Mar. 15, 2013, provisional application No. 61/852,367, filed on Mar. 15, 2013.

(51) Int. Cl.
*A61F 13/20* (2006.01)
*A61L 24/00* (2006.01)
*A61L 24/04* (2006.01)

(56) References Cited

U.S. PATENT DOCUMENTS

| | | | | |
|---|---|---|---|---|
| 2007/0021703 | A1* | 1/2007 | McCarthy | A61L 15/28 602/43 |
| 2007/0166387 | A1* | 7/2007 | Ahuja | A61K 9/1652 424/489 |
| 2008/0071207 | A1* | 3/2008 | de Luis | A61F 13/00017 602/47 |
| 2008/0132820 | A1* | 6/2008 | Buckman | A61B 17/1325 602/48 |
| 2010/0129427 | A1* | 5/2010 | Hen | A61L 15/24 424/445 |
| 2011/0077682 | A1* | 3/2011 | Gregory | A61F 13/00008 606/213 |
| 2011/0202016 | A1* | 8/2011 | Zugates | A61L 24/043 604/290 |
| 2012/0107439 | A1* | 5/2012 | Sharma | A61J 1/2093 425/4 R |
| 2014/0330221 | A1* | 11/2014 | Hen | A61L 24/0015 604/290 |

* cited by examiner

FOAM-BASED MEDICAL TREATMENTS

CROSS-REFERENCE TO RELATED APPLICATIONS

This application claims priority to U.S. Non-Provisional application Ser. No. 13/536,557 filed Jun. 28, 2012, titled "Foam and Delivery System for Treatment of Post-Partum Hemorrhage"; which claims priority to U.S. Provisional Application Ser. No. 61/554,181 filed Nov. 1, 2011. This application also claims priority to U.S. Provisional Patent Application No. 61/852,053 filed Mar. 15, 2013, titled "In-Situ Forming Gels for Medical and Cosmetic Purposes." This application also claims priority to U.S. Provisional Patent Application No. 61/852,225 filed Mar. 15, 2013, titled "Foam-Based Treatment of Bleeding in the GI Tract." This application also claims priority to U.S. Provisional Patent Application No. 61/852,367 filed Mar. 15, 2013, titled "Methods and Materials to Treat Junctional Hemorrhage."

FIELD OF THE INVENTION

The present invention relates generally to systems and methods for generating polymer foams within the GI tract to locate and/or control bleeding. The present invention further relates to systems and methods for generating polymer foams within non-compressible wounds to control and/or stop bleeding. The present invention further relates to the use of foams and gels for medical and cosmetic purposes.

BACKGROUND

Early stabilization of body fluid loss can be important in the treatment of wounds or diseases. For example, many injuries are treatable if effective hemorrhage control and operative surgical intervention are undertaken rapidly. In many situations, however, immediate access to surgical care is not available. Bleeding within the gastro intestinal (GI) tract is typically non-compressible, meaning that it cannot be treated by external compression or the application of tourniquets or topical dressings. In a large number of mostly older patients, diverticulum that form in the lower GI tract can lead to infection and bleeding. Such bleeding due to diverticulitis or other diseases can be severe, difficult to control, and may require emergent intervention. In addition to treating bleeding, locating sites of bleeding throughout the GI tract can be crucial to adequate care.

While the use of polymers in the treatment of medical conditions is known in the art, conventional materials and methods suffer from a variety of drawbacks. For example, many polymers irritate skin and/or internal tissues, and are not sufficiently biocompatible to be suitable for use inside a body cavity. Many polymers also lack suitable mechanical properties to be used inside the body; polymers that are too stiff may lead to discomfort or further injury, while polymers that are too soft may fail to provide adequate support for internal tissues. Moreover, previous approaches to locate and/or control GI bleeding require use of an endoscope and injection or cauterization techniques. These procedures are often complicated and require significant time and skill, especially in cases where bleeding is severe. Finally, the location of bleeding within the GI tract can be difficult to identify and require sophisticated imaging techniques to locate.

SUMMARY OF THE INVENTION

The present invention relates generally to systems and methods for generating polymer foams within the body to locate and/or control bleeding. The present invention further relates to systems and methods for generating polymer foams within non-compressible wounds to control and/or stop bleeding. The present invention further relates to the use of foams and gels for medical and cosmetic purposes.

Sites of bleeding that may be treated with the systems and methods of the present invention include, but are in no way limited to, hemorrhage within the gastrointestinal (GI) tract, junctional hemorrhage, bleeding in and around organs, bleeding from the sinuses and pelvic bleeding.

In one aspect, the present invention relates to systems and methods of using polymer foams. In another aspect, the present invention relates to formulations, compositions, and kits that are amenable to such systems and methods. In one embodiment, the system comprises a polymer and a bag that are inserted into the GI tract to locate and/or control bleeding. In one embodiment, the polymer formulation is deployed in the bag to produce a polymer foam to locate and/or control bleeding.

In another aspect, the present invention relates to a bag-in-bag system that is inserted into the GI tract to locate and/or control bleeding. In one embodiment, a polymer is deployed within the bag-in-bag system to produce a polymer foam to locate and/or control bleeding. In some embodiments, the polymer formulation and/or the foam have physical characteristics that are advantageous for facilitating compression and removal. Characteristics of the foam include high pore volume fraction, low compression-force-deflection (CFD) values, hydrophilicity, viscoelasticity, density, kinetics of foam formation, the ability to collapse (i.e., after a certain amount of time) and the ability to be filled with blowing gases.

In another aspect, the bag of the present invention includes features to facilitate the removal thereof from the body. In one embodiment, such features include one or more valve attachments, strings or clips. In another embodiment, such features include one or more coatings on the bag surface. In yet another embodiment, such features include and one or more energy sources in operative engagement with the bag.

In another aspect, the bag of the present invention comprises one or more therapeutic and diagnostic agents for deployment into the GI tract.

In yet another aspect, the present invention offers advantages not previously known in the art. For example, the polymers of the invention may be deployed into the GI tract to establish conformal contact with an actively bleeding injury without prior knowledge of the specific injury site(s).

BRIEF DESCRIPTION OF THE DRAWINGS

The above and further advantages of the invention may be better understood by referring to the following description in conjunction with the accompanying drawings, in which.

DETAILED DESCRIPTION OF THE PREFERRED EMBODIMENTS

Foams

Figure 1:
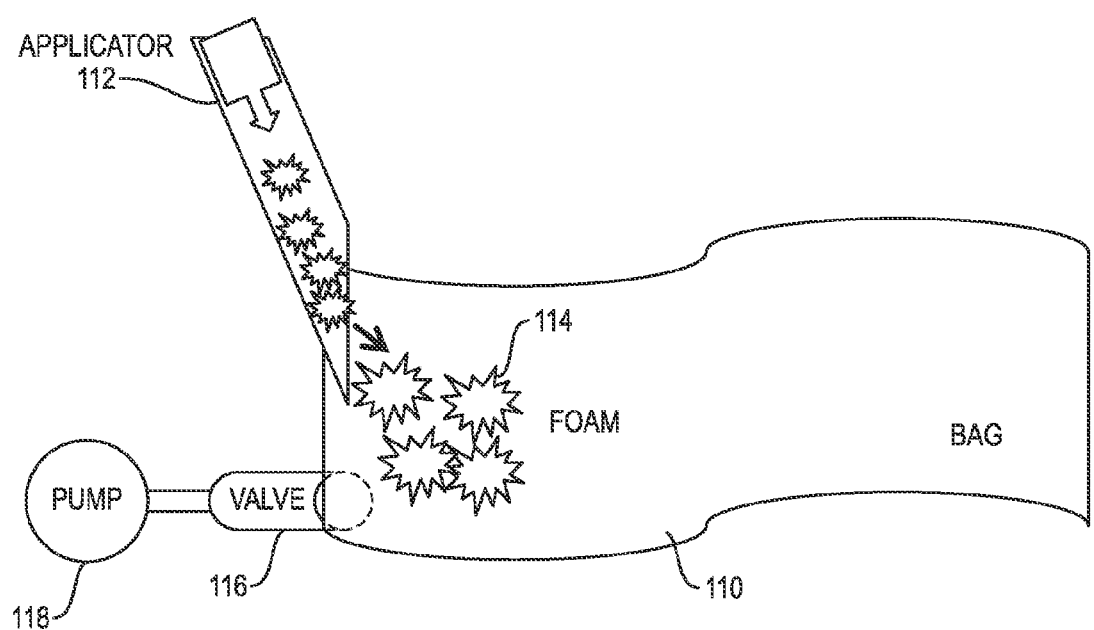
FIG. 1 illustrates the deposition of a polymer foam from an application into a tubular bag in accordance with one embodiment of the present invention.

The present invention relates generally to the use of foams for a variety of medical purposes. The terms "foam(s)", "foams" and "polymer foam" as used herein refers to any suitable pre-formed foam or foam formed in-situ from a one, two, or multi-part formulation (referred to interchangeably as polymers, polymer fluids, polymeric fluids, polymer solutions, polymer formulations, polymer materials and pre-polymers) as described in U.S. application Ser. No. 13/209,020, filed Aug. 12, 2011 and titled "In-Situ Forming Hemostatic Foam Implants," which is a continuation-in-part of U.S. application Ser. No. 12/862,362, filed Aug. 24, 2010 and titled "Systems and Methods Relating to Polymer Foams," which claims priority to U.S. Provisional Patent Application Ser. No. 61/236,314 filed Aug. 24, 2009, titled "Systems and Methods Relating to Polymer Foams," each of which are incorporated by reference herein for all purposes. The present invention also relates to United Sates application Ser. No. 13/815,910, filed Mar. 15, 2013 and titled "In-Situ Forming Foams with Outer Layer," which is a continuation-in-part of U.S. application Ser. No. 13/209,020, filed Aug. 12, 2011, which is a continuation-in-part of U.S. application Ser. No. 12/862,362, field Aug. 24, 2010 and which claims priority to U.S. Provisional Patent Application Ser. No. 61/236,314, filed Aug. 24, 2009; each of which are also incorporated by reference herein for all purposes. For example, a polyurethane foam may be formed in-situ from a one-part formulation consisting of an isocyanate-functionalized pre-polymer. Polymer fluids may additionally contain multiple polymer species, catalysts, surfactants, chain extenders, cross-linkers, pore openers, fillers, plasticizers, and diluents. For embodiments of the present invention in which foams are formed "in-situ," such foams are formed by the reaction of polymer(s) simultaneously with, or shortly after, delivery to a body cavity. In contrast, certain other embodiments of the present invention make use of pre-formed foams, which are formed prior to delivery to a body cavity.

In one aspect, the foams of the present invention are particularly suited for use within the body (e.g. biocompatible and/or bioabsorbable). In one embodiment, the foams do not induce adhesion with cells, tissues or organs and may be removed from the body using standard surgical procedures. In another embodiment, the foams are hydrophilic and may be dehydrated and inserted into a bag in a collapsed configuration. Addition of an aqueous solution such as water or saline to the dehydrated foam can cause foam to expand. Subsequent removal of the aqueous solution, for example using vacuum pressure (e.g., a pump) can return the foam/bag to the collapsed conformation. Foams may include a high volume fraction of cells and low CFD, such that the foam can be compressed and more easily withdrawn from the body. Foams may also include a highly resilient matrix such that they apply pressure when placed within a body cavity but can also compress to a reduced volume for easy removal. As used herein, a "cavity" is any open space within the body of a patient, including but not limited to body lumens, blood vessels, aneurysms, portions of the GI tract, wound cavities and spaces in and around body organs. Moreover, while many embodiments of the present invention are described with specific reference to the GI tract as examples, it should be appreciated that the systems and methods of the present invention are equally applicable to the treatment of other body cavities.

Foams may also be engineered to collapse/degrade after a pre-determined amount of time. For example, the polymers comprising the foam may include reversible cross-linkers such that foam is able to be selectively/controllably depolymerized. Depolymerization may be initiated by a variety of external stimuli, including solutions that contain chemically active compounds, enzymes, ultrasound forces, radiofrequency forces, light or vacuum. For example, the polymer foam may contain anhydrous bonds that can be hydrolyzed. Reversion to an uncross-linked state may allow the foam to be more easily removed from body. Other foams may comprise structures that are only stable when their pores are filled with gas (e.g., air) and cannot support an expanded shape when the gas pressure decreases below a certain threshold.

In some embodiments, the foams of the present invention may be described as "lava like" during their formation phase, in that they are viscous, yet flowable, and harden from the exterior surface towards the interior. The external skin of the foam rapidly forms as a robust, balloon-like outer layer upon contact with blood or water to encase the inner polymer formulation. This promotes material cohesion and resists deformation and movement outside the targeted area, including for example, migration into collateral vessels. The external skin of the foam may deform during expansion to expose at least a portion of the inner polymer formulation, which may then react upon contact with the external environment to reform a new external skin surface. As used herein, the outer layer of the foam may be referred to as a "skin" that consists of a thin exterior layer that is harder (e.g., more solid, less flowable) than the material contained within that outer layer. Additionally, the skin may be characterized as "robust" due to mechanical properties (e.g., strength, toughness, etc.) that are different, at least for some period of time, than the material contained by the skin. The formulation within the interior tends to harden via the same process as the skin, albeit more slowly.

The skin may form rapidly to produce a material that is not cohesive in-situ, resulting in a continuous, packable polymer, which may tend to form coils. Continued extrusion of the formulation out of a delivery device such as a catheter or micro-catheter may allow a user to create long/sustained/continuous coils to partially or completely fill an aneurysm or other body cavity. In one embodiment, this space may be filled with an aneurysm coil or other medical implant and an in-situ forming foam. In another embodiment, this space may be filled with an aneurysm coil that is coated with a material that expands to form a foam coating in-situ. The continuous/long aspect ratio can prevent such coils from entering collateral vessels to a significant degree.

In certain embodiments, foams may be formed by a fast cross-linking reaction that can be surface triggered by water in-situ. For example, multi-functional moisture sensitive silanes are susceptible to such reactions; especially when formulated with tin, titans or other metal-organic catalysts. For example, a one-part cross-linking system may be created by a two-step process in which hydroxyl containing siloxanes (either silanols or carbinols) are first reacted with an excess of multifunctional silane containing acetoxy, oxime, alkoxy (e.g., methoxy, ethoxy), isopropenoxy, amide, amine, aminoxy, or other functional groups containing silane with the hydrolytically susceptible Si—O—C bond. The resulting pre-polymers have multiple groups that are susceptible to hydrolysis. In the second step the pre-polymers are exposed to water in-situ to provide a rapidly cross-linking elastic solid. This reaction proceeds from the outside-in, resulting in a quickly formed outer skin and, in some cases, the formation of the foam into a coil-like configuration. The slow permeation of water through this outer skin allows the material inside of the skin to cure more slowly.

Alternative reaction triggers (e.g., blood, saline, tissue or other biological matrices) can be introduced to slowly cure the material inside of the skin. For example, the proteins and/or pH of the blood can support coil formation and prevent coil sticking (i.e., self-agglomeration) by modifying the rate of the skin-forming reaction. Solidification of the interior portions of foams within the exterior skin may also be controlled by altering the permeability of the material to a given solidification trigger (e.g., water) by adjusting the hydrophobicity of the material.

Additionally, hydride functional (Si—H) siloxanes or isocyanate functionalized carbinols can be introduced into silanol elastomer formulations to generate gas and produce expanding foamed structures. Expansion of the material increases the size of the formed coil, thereby effectively decreasing the embolization potential of the coil. Expansion can also increase the size of the material thereby adding porosity and generating sealing pressure without requiring the delivery of additional material. Additional formulation ingredients such as surfactants may be used to alter the impact of generated gas on porosity and expansion.

In another aspect, isocyanate-containing pre-polymers may be used to generate in-situ forming coils. Isocyanate groups are relatively unstable when exposed to water and moisture. One-part isocyanate based cross-linking systems may be generated by a two-step process. In the first step, polyols, diols, diamines, polyamines, diepoxides, silanols, carbinols or polyepoxides are capped with aliphatic or aromatic diisocyanates such as isophorone diisocyanate (IPDI), hexamethylene diisocyanate (HDI) and methylene diphenyl diisocyanate (MDI). Additionally, multifunctional isocyanates such as HDI biuret, HDI trimer, and polymeric MDI can be combined with diols or diamines. The resulting pre-polymers have multiple distant isocyanate groups that are able to react with the water and amines present in blood. In the second step, the pre-polymers are exposed to in-situ blood resulting in rapid cross-linking and foam formation. This reaction may be triggered by water to proceed from the outside-in to form a porous outer skin core structure (e.g., lava-like shell) that promotes coil formation. The expansion of these materials can generate large diameter coils from a delivery device with a small cross-sectional area. Such materials may be used to form stand-alone foaming or gelling coils. Multiple materials may also be combined such that one material is coaxially formed on top of another material. For example, a coaxial delivery device may deploy a coil forming formulation surrounded by a highly expandable coating formulation. The coil forming formulation and coating formulation may be from different chemistry classes. The two formulations may be selected to be immiscible such that upon delivery the individual formulations phase separate (e.g., oil miscible and water miscible formulations) to naturally form a coaxial structure. In yet another embodiment, two-part formulations may be designed such that the two formulations are not fully miscible. For example, a surfactant system may be used to formulate the two-part formulation into a single stable emulsion. Such an emulsion may be delivered via a single chamber delivery device that does not require mixing. These emulsions can be destabilized by shear forces during delivery (e.g., interaction with the catheter was during delivery) or by in-situ factors such as pH, temperature and/or ionic strength such that the internal phase of the emulsion spills out and triggers the reaction with the external phase resulting in in-situ foam formation.

Additionally, any of the foams (or gels) of the present invention may be further formulated to be radiopaque, fluorescent, or otherwise visible by imaging techniques known to those skilled in the art. For example, radio-opacity may be imparted by incorporation of iodinated contrast materials, barium sulfate, metal particles such as tantalum or titanium, etc. The foams or gels formed may be bioresorbable, non-absorbable, biocompatible or biodegradable. In some embodiments, biodegradability is achieved by the use of hydrolytically or enzymatically degradable polymers such as polyglycolic acid (PGA), polylactic acid (PLA), PLGA, polycaprolactone (PCL), polydioxanone, polyanhydrides, polyorthoesters, or various random and block copolymers. Additional ingredients may be also be added to the foams (or gels) to adjust their density and/or contact angle with blood, tissue, or other biological matrices.

The foams (or gels) of the present invention may further comprise agents known to enhance the endogenous blood coagulation process such as natural clotting factors (e.g., thrombin, fibrinogen/fibrin, factor X/Xa), chitin/chitosan, cellulose derivatives, alginate, gelatin, zeolites, and water-absorbent materials. These coagulation agents may be dissolved or suspended in the formulation or added as a separate phase at the time of delivery.

While certain embodiments present herein relate to in-situ forming foams or gels, the systems and methods of the present invention may also include the use of pre-formed material such as pre-formed foams, gels, deformable clays, meshes or related particles. All of the considerations relating to in-situ forming foams or gels present herein, including the use of pro-coagulants, tissue-binding ligands and adhesives, and biodegradable polymers also apply to pre-formed materials. Pre-formed materials may be used alone or in combination with a bag or balloon of the present invention. As used herein, "pre-formed" refers any material prepared outside of the body prior to insertion, delivery, or installation into the body, including for example a wound, organ or other body cavity. Pre-formed materials may be provided in a variety of shapes (e.g., rod, tubes, spheres, discs, polygons, ellipsoids and the like), including those formed by a mold or individually formed in the hands of a user. Preferable shapes for pre-formed foams include those with an aspect ratio greater than one to facilitate sequential, end-to-end removal. Additionally, pre-formed materials may be provided as thin strips or sheets, and may be perforated to optimize wound packing. Pre-formed foams may also contain radiopaque agents to facilitate identification and removal.

Gastrointestinal Tract Bleeding

In one aspect, the present invention relates to systems and methods for locating and/or controlling bleeding within the GI tract. In one embodiment, the present invention relates to the generation of polymer foams, deployment of polymer foams within a bag for placement within the GI tract and subsequent removal of the bag from the GI tract. As used herein, the term "bag" refers to any suitable bag, sack, or other open- or closed-ended container, and can be made from non-compliant, semi-compliant or compliant materials (e.g., latex, nylon, polyurethane and ePTFE). These bags allow rapid and accurate deployment of polymer foams for a variety of medical applications. Including, for example, to control hemorrhages within the GI tract by exerting pressure on the intestinal wall as the foam expands. The polymer foams of the present invention may be placed in direct or indirect contact with numerous a site(s) of bleeding within the body including, for example, tissues (e.g., injured tissue), internal organs and the like.

In one aspect, the present invention relates to a method of preventing and/or limiting the movement of bodily fluids (e.g., blood) by forming a foam within the GI tract. Such foams may have physical characteristics that are advantageous for preventing or limiting the movement of a bodily fluid, such as the degree of expansion of the foam, the density of the foam, the softness or stiffness of the foam, the viscosity of the formulation, the ability to absorb both high and low volumes of blood and/or water (which can be very important for transport and hemostasis) and the kinetics of foam formation from the formulation. For example, the foam may promote hemostasis when applied near a hemorrhage site. As used herein, "hemostasis" (the opposite of "hemorrhage) refers to any process that causes bleeding to slow or stop (e.g., to keep blood within a damaged blood vessel). Hemostasis is the first stage of wound healing and typically proceeds in three major steps: i) vasoconstriction, ii) temporary blockage by a platelet plug and ii) blood coagulation or clotting that seals the wound until the tissues are repaired.

In one aspect, the invention relates to a polyurethane foam that is formed in-situ from a one-part formulation. The formulation may include a pre-polymer that is capped with an isocyanate compound such as hexamethylene diisocyanate (HDI), toluene diisocyanate (TDI), methylene diphenyl diisocyanate (MDI), or isophorone diisocyanate (IPDI) with a functionality of preferably between 2.0-4.0. The preferred viscosity of the one-part formulation is 1-3,000 cP, and more preferably 1-1,000 cP. The formulation may also include catalysts, surfactants, diluents, cross-linkers and chain extenders. The reaction that forms the foam from the one-part formulation can be triggered by initiators such as moisture or heat, including body heat or heat provided from an appropriate delivery system. The bag may be flushed with an aqueous phase (e.g., water) prior to deployment of the one-part moisture formulation to provide a wet environment to initiate foaming. The reaction may also be triggered by a time sensitive cross-linker. For example, addition of a specific amount (i.e., concentration) of cross-linker to the formulation prior to delivery to the patient can establish a pre-determined period (e.g., time window) during which the operator may deploy the formulation before in-situ cross-linking occurs. Blowing agents (e.g., air, carbon dioxide or related auxiliary blowing agents) may also be entrained within the formulation prior to delivery to the patient or introduced during in-situ delivery as a component of the one-part formulation.

In another aspect, the present invention relates to a polyurethane foam that is formed in-situ from a two-part formulation. The first part of the formulation may include an isocyanate compound such as hexamethylene diisocyanate (HDI), toluene diisocyanate (TDI), methylene diphenyl diisocyanate (MDI) or a mixture of MDI isomers, polymeric MDI, isocyanate-functionalized pre-polymer, or a polymeric isocyanate having a functionality of preferably between 2.0-3.0). The second part of the formulation may include a hydroxyl-functionalized polymer (polyol). This polyol phase can include multiple polyol species, catalysts, surfactants, chain extenders, cross-linkers, pore openers, fillers, plasticizers and water. The viscosity of the first and second parts of the formulation is preferably 1-3,000 cP, and more preferably about 2,400-2,600 cP. Blowing agents (e.g., air, carbon dioxide or related auxiliary blowing agents) may also be entrained within the isocyanate and/or polyol phases prior to delivery to the patient or during in-situ delivery as a component of the two-part formulation.

Bags

In one aspect, the present invention relates to polymer foams that are deployed into the GI tract within a bag. In one embodiment, a polymer solution is introduced into the bag such that the in-situ polymer foam forms within the bag. In another embodiment, the foams are deployed into the bag in one or more pre-formed foam shapes (e.g., components), which are preferably attached to one another using a variety of suitable attachment devices (e.g., strings, clips or similar structural elements). More preferably, the foam shapes have an aspect ratio greater than one and are attached end-to-end to facilitate removal. The polymer foams expand within the bag to conform to, and exert pressure on, the intestinal wall to control a hemorrhage. As shown in FIG. 1, an applicator 112 with a handle that remains external to the GI tract is used to insert one or more foam components 114 into tubular bag 110 such that it expands and conforms to the shape of the intestinal wall. To remove the bag from the GI tract pump 118 connected to valve 116 may be used to create a vacuum (i.e., remove air) from the bag such that the foam (whether pre-formed or in-situ formed) within the bag collapses to a more condensed (i.e. smaller) configuration. In another embodiment, the pump and valve may be used to collapse the foam such that the foam may be removed from the bag, followed by the removal of the empty bag from the GI tract.

Figure 2C:
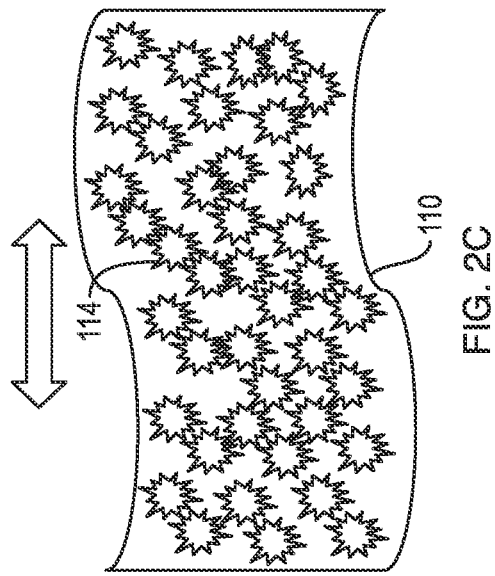
FIGS. 2A-C illustrates the deployment order of a polymer foam inside a bag of the present inventions. Upon introduction of foam the unexpanded bag (2A) expands first in the axial direction (2B) and then in the radial direction (2C).
Figure 2B:
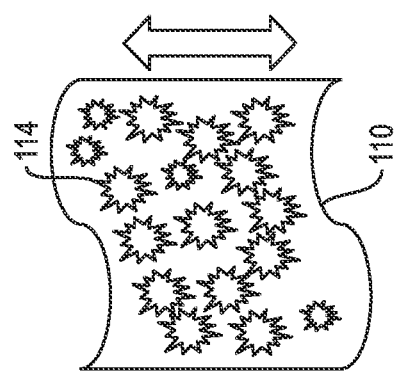
Figure 2A:
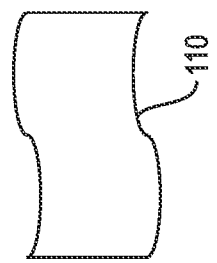

In one aspect, the present invention relates to a variety of types of bags. As shown in FIG. 2, the bag may be designed such that the unexpanded bag (2A) first expands radially to a pre-specified maximum diameter (FIG. 2B) and then expands axially (FIG. 2C). Alternatively, the bag may be manufactured with multiple sections along its length that collapse in an accordion-like fashion. These collapsed sections are retained in proximity to one another using an adhesive or other attachment means. As the proximal-most section of the collapsed bag is filled, the bag preferably expands in the radial direction due to the adhesive forces between the collapsed sections. Upon complete expansion of the proximal section in the radial direction the pressure within the bag is sufficient to overcome the adhesive force of the adjacent collapsed section, thus allowing the foam to fill the next section. This process can continue until the last segment has been expanded or the user stops introducing additional foam. Additionally, individual segments of the bag may be separated by throttles or valves which open (e.g., rupture) at pre-specified pressures, thereby allowing the foam to fill each segment radially before the next segment expands. For example, this design may prevent excessive axial pressure from being exerted on any given section of the intestinal wall while still establishing good conformal contact between the implant (e.g., bag) and the wall of the GI tract. The pressure exerted on the intestinal wall may be further optimized (i.e., increased or decreased) by introducing and/or removing suitable gases into the bag.

Figure 3:
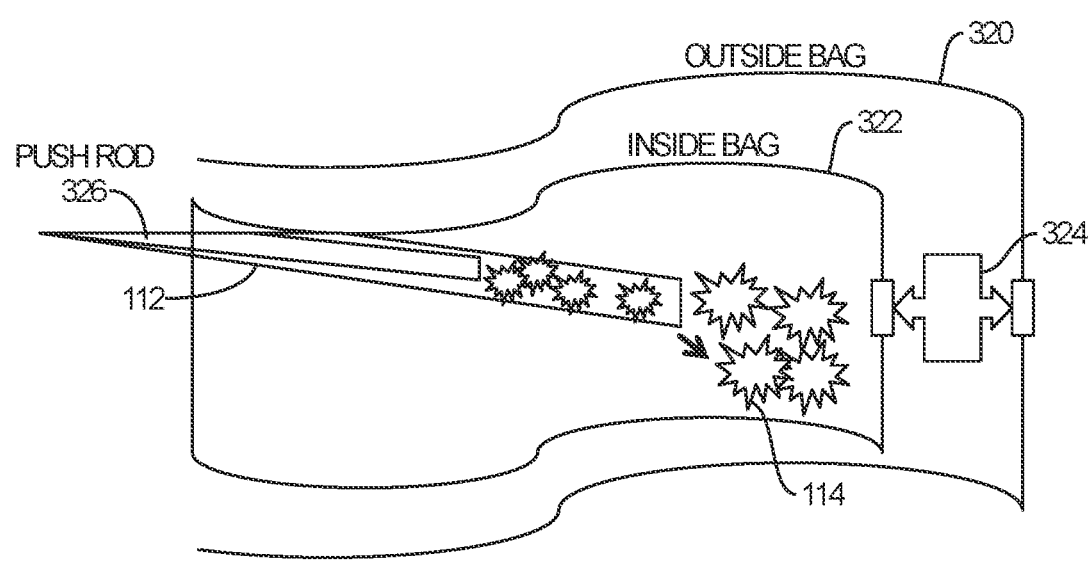
FIG. 3 illustrates a bag-in-bag system in accordance with one embodiment of the present invention.

In one aspect, the present invention relates to a two-layer bag-in-bag system that includes an inner (inside) bag 322 within an outer (outside) bag 320, as shown in FIG. 3. Examples of such systems are described in co-pending and commonly-assigned application Ser. No. 13/536,557, entitled "Foam and Delivery System for Treatment of Post-Partum Hemorrhage" to Sharma et al., which is incorporated herein by reference for all purposes. The bag-in-bag system may further include a mechanical attachment 324 (e.g., a clip or string) between the outer 320 and inner 322 bags to facilitate removal of the outer bag 320 by pulling on the foam-filled inner bag 322. For example, foam 114 is deployed into the inner bag 322 of the bag-in-bag system placed within the GI tract. Upon completion of the procedure within the GI tract, the inner bag 322 is pulled out through the inside of the outer bag 320; the outer bag 320 (which is connected to the inner bag 322) then follows the inner bag 322, turning itself inside out during the process. This design feature provides an important benefit to the patient since no sliding motion occurs between the bag(s) and the patient's tissues.

As with the single-bag system (FIG. 1), the bag-in-bag system may be used in conjunction with both pre-formed foams and/or in-situ forming foams. A delivery system comprising a small diameter tube or catheter applicator 112 may be used to insert the one or more pre-formed foam shapes into the bag, as shown in FIG. 3. In another embodiment, a concentric push rod 326 may be used to deploy the pre-formed foam into the bag as the outer tube applicator 112 is held in place or retracted. In one embodiment, the pre-formed foam shapes may comprise a viscoelasticity gradient such that the distal most shape expands the slowest while the proximal most shape expands the fastest.

Figure 7A:
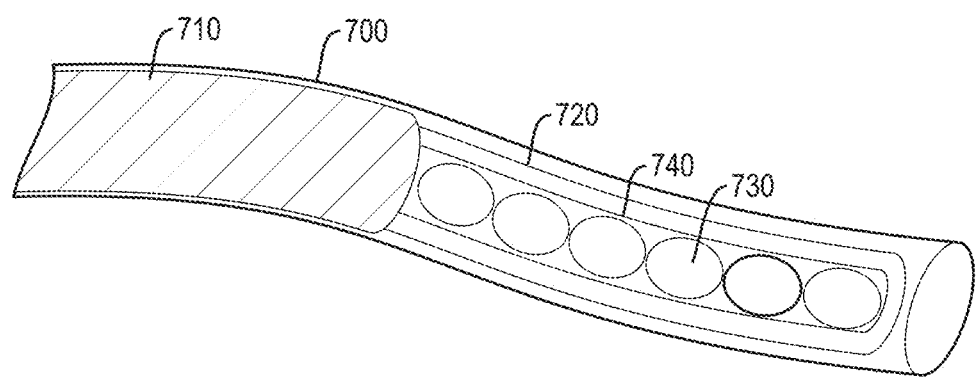
FIGS. 7A-B depict the bag-in-bag system containing collapsed pre-formed foam components within a delivery device (7A) and upon delivery into a body cavity (7B).
Figure 7B:
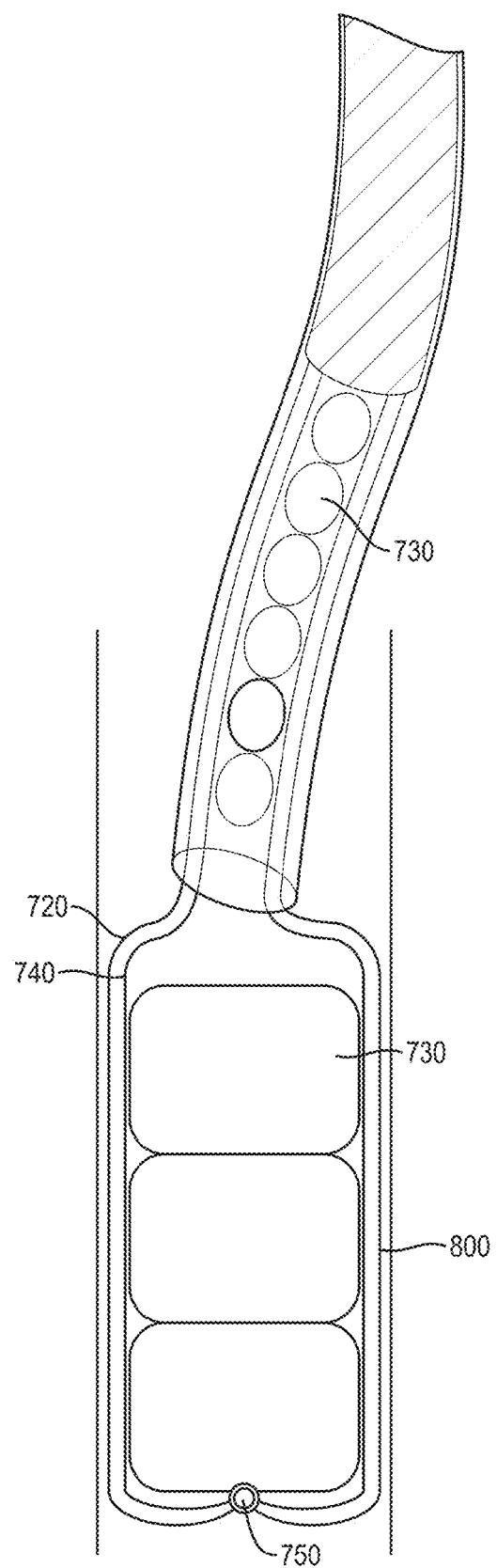

In one embodiment as illustrated in FIG. 7A, multi-part pre-formed foam components 730 are retained in a collapsed configuration within the inner bag 740 of the bag-in-bag system positioned within a suitable delivery device 700 (e.g., delivery tube, catheter, endoscope, hysteroscope, laproscope etc.). A push rod or fluid column 710 may be used to advance the bag-in-bag system along the length of the delivery device. As illustrated in FIG. 7B, the delivery device is positioned within a cavity 800 of a patient, and the bag-in-bag system is advanced through the open end of the delivery device. As the multi-part pre-formed foam components 730 advance out of the delivery device they expand and conform to the shape of the cavity 800. In one embodiment, the most distal pre-formed foam component is attached to the inner 740 bag.

In one embodiment, the bag is porous or perforated such that it directs the expansion of the foam until a critical pressure is reached. Any foam extending beyond the bag (i.e., through the pores) remains mechanically connected to the foam within the bag such that an intimate and conformal contact is maintained between the foam and the intestinal wall while still allowing the foam to be removed along with the bag. For example, perforations in the bag are of sufficient size that the cross-sectional area of the foam connecting the inside and outside of the bag portions is sufficient to withstand forces on the outer foam during removal. Stronger (i.e. denser) foams may require this cross-sectional area to be smaller, while weaker (i.e. less dense) foams may require the cross-sectional area to be larger. In one embodiment, pre-formed hydrophilic foams may also be used as a coating on the external surface of the bag to conform the intestinal wall. Such foams may be dehydrated and expand upon contact with liquid (e.g., blood) to further conform to a contact surface (e.g., intestinal wall).

In one embodiment, a feedback noting scale or other system may be provided to indicate the distance (i.e., depth) of travel into the GI tract. For example, a string with gradation markings along its length may be attached to the tip (applicator, tube, or clip) of the bag such that some marks remain visible outside the patient. Additionally, the bag itself may have gradations on its surface to indicate how far the bag has been positioned inside the GI tract.

In one embodiment, a delivery system may be used in which the bag rests over the tip of a nozzle containing the foam (in-situ formed or pre-formed) to control how much foam is dispended. Pressure exerted against the nozzle advances/deploys the foam when the tip is inserted into the GI tract of the patient. In another embodiment, the outer surface of the bag may be pre-lubricated. In yet another embodiment, a lubricant may be applied through a natural body orifice, or through a surgical incision is made in a patient.

Removal

Upon completion of their use within the body, the foam(s) and/or a bag(s) of the present invention are preferably removed. In one embodiment, agent(s) may be introduced into the bag to liquefy the foam. For example, if the polyol backbone of the foam is largely composed of easily hydrolysable anhydride segments an aqueous wash may be flushed through the bag to degrade the foam. In this case, the bag materials would be selected to be water impermeable, semipermeable or permeable to provide control over how much water or moisture from the body contributes to foam degradation. An external energy source (e.g., ultrasound, radiofrequency, vacuum, pressure, or combinations thereof) may also be applied to the bag to collapse or otherwise break the cell walls between individual pores of pre-formed or in-situ formed foams to facilitate their removal. The external energy source may result in the escape of gases to collapse of the foam. A vacuum may also be applied to collapse the foam and/or rupture the cell walls, either alone or in combination with other forces. For example, the proximal end of the bag may be sealed with a tube connecting the inner chamber to a pump (e.g., manually or mechanically powered) that supplies a vacuum force to collapse the foam. At least one valve may be disposed in the tube to enable a user to control pressure in the bag and collapse the foam by actuating the pump (e.g., negative pressure drawn on the attached syringe).

Figure 8A:
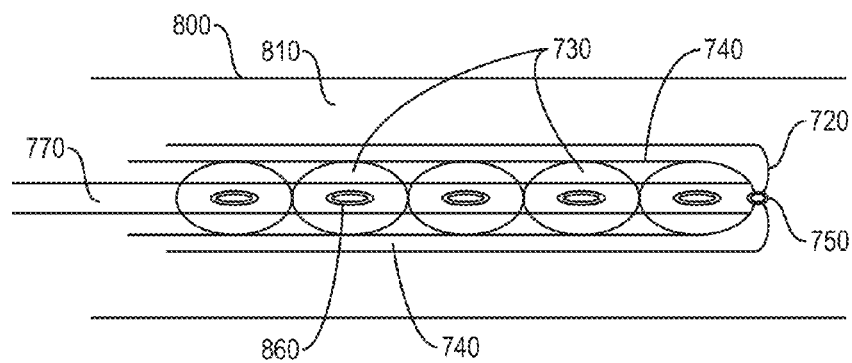
FIGS. 8A-D depict embodiments of the bag-in-bag system within a body cavity. The bag-in-bag system containing multi-part pre-formed foam components is shown in a collapsed (8A) and expanded (8B) configuration. Multi-part pre-formed foam components may be attached end-to-end to facilitate removal from the body cavity (8C, D).
Figure 8B:
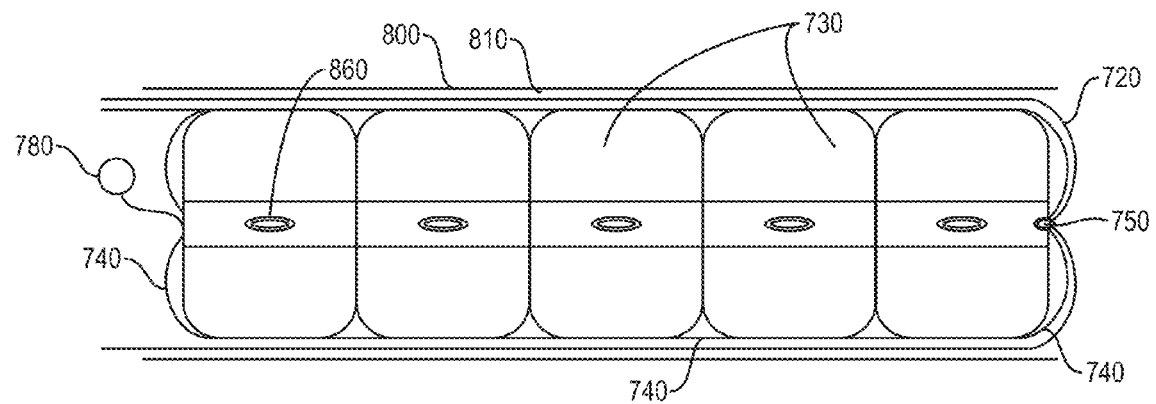
Figure 8C:
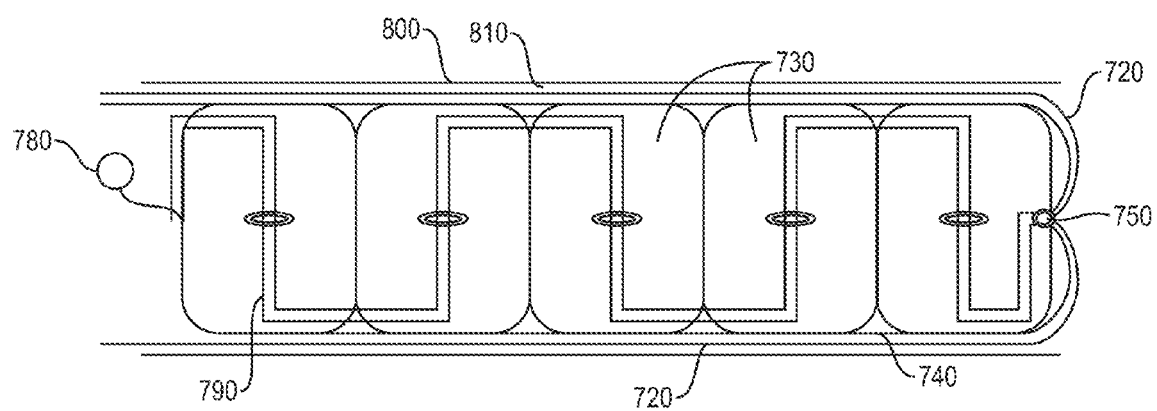
Figure 8D:
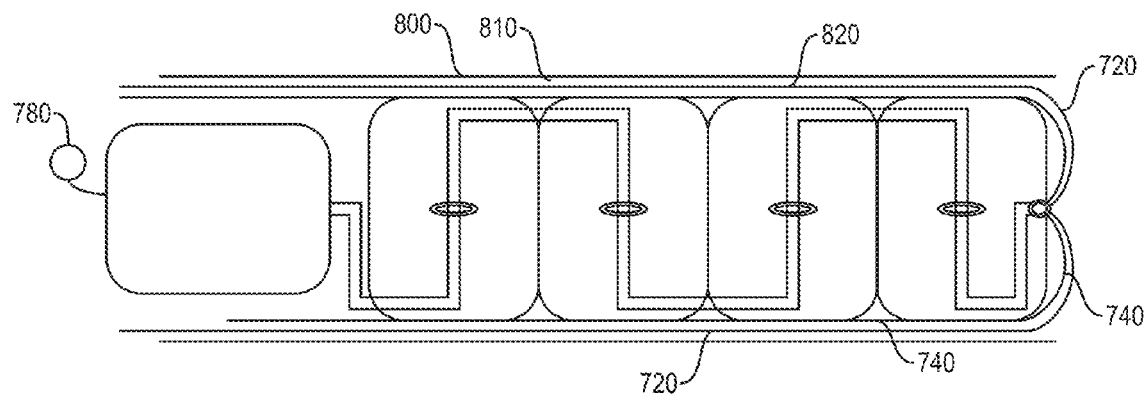

FIGS. 8A-8D illustrate various embodiments by which the bag-in-bag system is removed from a body cavity. FIG. 8A depicts the bag-in-bag system positioned within a lumen 810 in a collapsed configuration. The multi-part pre-formed foam components 730 are contained within the inner bag 740. In a preferred embodiment, the inner 740 and outer 720 bags are attached to each other, such as by being adhered together by an adhesive or by being mechanically attached by a connector 750, which may be a clip, tether, grasping device, or other mechanical attachment means. In some embodiments, the inner 740 and outer 720 bags are actually part of the same bag structure that is twisted or otherwise delineated at the distal end of the inner bag 740 and turned back upon itself to form the outer bag 720. Openings 760 allow unreacted foam formulations to be dispensed into individual segments of the inner bag 740. In another embodiment, foam formulations may be injected via tube 770 that extends the length of the inner bag. FIG. 8B depicts the bag-in-bag system in an expanded conformation within the lumen 810. A string 780 attached to the inner bag 740 allows the bag-in-bag system to be withdrawn from the patient by pulling the inner bag 740 through the center of the outer bag 720. The outer bag 720, which is connected to the inner bag by connector 750, collapses and follows the inner bag without direct sliding contact against the inner surface of the body cavity 800. FIG. 8C depicts an embodiment in which each of the multi-part pre-formed foam components are attached end-to-end by a connector 790. Pulling the string 780 allows the multi-part pre-formed foam components to be sequentially removed from the lumen, as depicted in FIG. 8D. The ability of each pre-formed foam component to rotate to a position that exerts less pressure (or no pressure) on the lumen may further reduce the amount of force required to remove the bag-in-bag system from the patient, thereby reducing discomfort and trauma to tissue surfaces.

Figure 9:
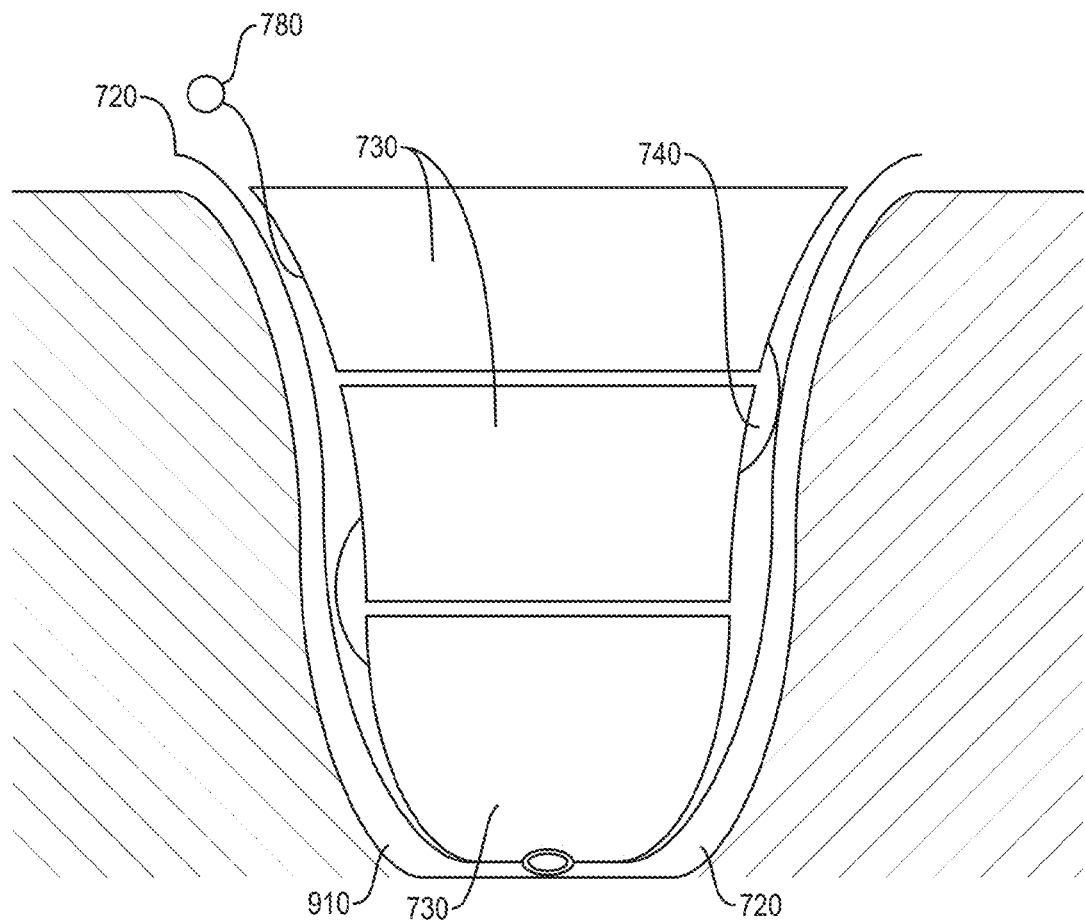
FIG. 9 depicts the bag-in-bag system with multi-part pre-formed foam components attached end-to-end deployed within a wound cavity.

FIG. 9 depicts the bag-in-bag system positioned within a wound cavity 910 with the inner 740 and outer 720 bags attached to each other at connector 750. The multi-part pre-formed foam components are attached in an end-to-end configuration such that they may be sequentially removed by pulling on string 780.

Bleeding Site Diagnosis

In one embodiment, the bags of the present invention may be coated on their outer surface(s) with a foam that absorbs and coagulates blood in order to identify and/or diagnose sites of bleeding. For example, spots of coagulated blood on the outer surface of a bag inserted into the GI tract may be used to identify/localize sites of bleeding. Gradation markings along the bag may be used to correlate regions of blood coagulation to the insertion distance of the bag, thereby establishing the anatomical location of the bleeding. A user (e.g., surgeon) may use such information to identify segments of GI tract that are bleeding and/or to identify sites for future surgical intervention. Highly porous foam coatings on the outer surface of the bag may also promote clotting at the site of bleeding. Similarly, negatively charged agents such as chitosan may be incorporated into/onto the outer surface of the bag to promote clotting at the site of bleeding. Other pro-coagulation agents (e.g., thrombin, chitosan and kaolin) may also be incorporated into the foam, bag or material on the surface of the bag.

In one embodiment, the outer bag of the bag-in-bag system may be perforated or otherwise allow fluids or materials infused between the inner and outer bags to contact the intestinal surface. For example, foams comprising therapeutic or diagnostic agents (e.g., thrombin, chitosan, kaolin, $^{99m}$Tc sulfur colloid and $^{99m}$Tc-labeled red blood cells) may be used to expand the inner bag and infuse into the space between the inner and outer bags. Alternatively, pro-coagulant or anti-fibrinolytic agents (e.g., thrombin or tranexamic acid) may be infused into/onto the outer surface of the outer bag, or introduced along with the bag at the time of insertion within the patient. In yet another embodiment, the bag may be porous such that such pro-coagulant agents located within the bag may pass through its surface to contact the intestinal wall.

In one embodiment, the foam may be radiopaque such that x-ray imaging can determine the location of the bleeding. In another embodiment, the foam may exhibit sufficient ultrasound or MRI contrast such to allow imaging of the foam's location within the GI tract.

The approaches described above may also be used in other applications, such as: placement in the fallopian tubes or vas deferens for female or male sterilization, controlling bleeding or post-surgical packing of sinuses of other body cavities or locations, permanent or temporary displacement of tissues or organs to prevent damage during surgical, radiation, cryoablation, thermal ablation or other procedures or treatments. For example, in female sterilization multiple pre-formed disks can be attached end-to-end using an inner bag. The expanded disk diameter is preferably between 1 and 5 mm. The disk thickness if preferably between 0.5 and 3.0 mm. A number of disks are stacked in the implant to provide an implant of total length up to 4.0 cm. The inner is bag attached at one end to the inside end of an outer bag. A hysteroscope with a 5 French working channel provides access and a catheter is inserted into a Fallopian tube. An inner push catheter or fluid is used to expel the foam implant once the catheter tip reaches the desired position in the Fallopian tube.

In-Situ Forming Gels for Medical and Cosmetic Purposes

Previous attempts to use polymers for medical applications have suffered from a number of drawbacks, including the lack of suitable mechanical properties for use inside the body and/or inability to be delivered into a closed cavity or otherwise reach inaccessible sites. For example, many polymers are too hard and lead to discomfort or further injury while other polymers are too soft and fail to provide adequate support for internal tissues. Some polymers include components that must be stored at cold temperature to prevent degradation, solidification, gelation, or similar change in their desired mechanical or chemical properties. Other polymers do not gel or solidify at body temperature and must be gelled or solidified prior to insertion into the body.

In one aspect, the present invention relates to polymer fluids suitable for delivery into physiologic, pathophysiologic, or synthetic spaces inside the body where they subsequently solidify, gel or otherwise become immobilized for a variety of medical and/or cosmetic applications. For example, a polymer fluid delivered into a space resulting from surgery or infection can fill that space once the fluid gels. Polymer fluids may also be delivered into the body to augment or change a physical appearance for cosmetic purposes upon solidifying. Non-limiting examples of medical applications for the polymer fluids and gels of the present invention include filling aneurysms, eye implants and cartilage replacement. Non-limiting examples of cosmetic applications for the polymer fluids and gels of the present invention include breast implants, calf implants, cheek implants, chin implants and buttocks implants.

In another aspect, the present invention relates to methods of introducing polymer fluids into the body of a patient such that the fluid gels to stabilize a physiological element and/or medical device. Such a gel may be formed by the interaction of two (or more) polymer fluids that are delivered to a patient simultaneously or sequentially. Gels may also be formed by the interaction of the polymer fluid with an aqueous environment (e.g., blood, water, and/or saline). Additionally, a gel may be formed following the delivery of a physiologic force or stress to the polymer fluid.

In another aspect, the present invention relates to polymeric fluids that are injected or deposited into the desired location into the body of a patient, for example by using a syringe, catheter or related device comprising a hollow bore. As used herein, a polymer fluid is described as being "injected", "deposited", "delivered" or "administered" to indicate the placement of the fluid a target location within a patient's body using any suitable means. Depending on the viscosity of a given polymer fluid, a hand-powered syringe-assist, pneumatic pressure pump, or other device may be used to increase the flow rate and ease injection of the polymer fluid. A multi-barrel syringe may be used to simultaneously inject multiple polymer fluids. Adequate mixing of multiple polymer fluids may include a mixing nozzle, such as a static mixing nozzle, mounted onto the multi-barrel syringe cartridge. Alternatively, multiple polymer fluids may be combined prior to being injected or injected sequentially.

In yet another aspect, the present invention relates to the use of polymer fluids and gels in conjunction with a bag to direct the flow and/or constrain the shape of the gels. For example, such gels may be used to apply pressure to at least a portion of an organ such that movement of a fluid within that organ is controlled. As used herein, the term "balloon" is used synonymously with the term "bag" (as described above) to refer to any suitable container bag, sack or container into which the polymer fluids and gels of the present invention may be placed. The bag may be compliant, semi-compliant, or non-compliant (i.e. sized by the operator to fit the target lumen); elastic or non-elastic; and/or biodegradable or non-biodegradable. As used herein, the term "biodegradable" is used synonymously with "bioabsorbable" and "bioerodible." The polymer fluid or gel may be introduced into the balloon in a one- or two-step process. In the two-step process, the second step can occur before or after introduction of the balloon into a body cavity or lumen.

As used herein, a material is described as a "fluid" if it is flowable, as for example, fluid, semi-solid, and viscous materials. As used herein, a fluid is said to "gel" upon undergoing a chemical and/or physical change that results in the formation of a solid, a semi-solid or a more viscous fluid. Fluids may comprise a singular polymer fluid or a plurality of polymeric fluids; preferably as many as to ten polymeric fluids, more preferably fewer than four polymeric fluids, and even more preferably fewer than three polymeric fluids.

Gels of the present invention may be generated by the cross-linking of polyols with multifunctional isocyanates. Polyols suitable for use in such embodiments include polyether- and polybutadiene-based polyols. Polyols of particular interest include polypropylene glycol (PPG) and polyethylene glycol (PEG), as well as random and block co-polymers thereof. Also suitable for use are polycarbonates, polybutadienes, and polyesters. While diols, triols, and tetrols are preferred, multifunctional polyols with any suitable number of arms may be used. Molecular weights between 100 and 10,000 Da are preferable, with molecular weights up to 6,000 Da being most preferred. Blends of polymers with different molecular weights, degrees of branching, and composition are also contemplated. Commercial polymers of particular interest include polypropylene glycols (425, 1200 Da), polyethylene glycols (200, 400, 600, 1000, 2000, 3000 Da), Pluracol products (355, 1135i, 726, 816), Arch Poly-G 30-240, Poly-G 76-120, Poly-G 85-29, trimethylolpropane ethoxylate (TMPEO, 450, 1014 Da), pentaerythritol ethoxylate (797 Da), UCON 75-H-1400, UCON 75-H-9500, dipropylene glycol, diethylene glycol, tripropylene glycol, triethylene glycol, tetrapropylene glycol, and tetraethylene glycol. The formulations of the present invention may also comprise amine catalysts in amounts up to 10 wt % (w.r.t. polyol), and preferably up to 1 wt % (w.r.t. polyol). The formulations of the present invention may further comprise diluents up to 300 pphp (preferably up to 250 pphp and most preferably up to 100 pphp). Isocyanates of the present invention may include Mondur MRS2 (Bayer), Lupranate MI, M20 (BASF), and related mixtures of methylene diphenyl diisocyanate (MDI). Still other isocyanates may include toluene diisocyanate (TDI), hexamethyline diisocyanate (HDI), lysine isocyanate (LDI), isophorone diisocyanate (IPDI), isocyanate-functionalized polymers thereof, polymeric MDI (with functionality preferably between 2.0-3.0), or mixtures thereof. In certain embodiments, the viscosity of the fluid or fluids is less than 10,000 cP, preferably less than 2,000 cP, more preferably less than 100 cP, and even more preferably less than 50 cP. Examples of polymer systems used in accordance with certain (non-limiting) embodiments of the present invention are listed in Table I.

TABLE I

Gel times and temperature increases of two-part gelling systems

| | Part A | | Part B | | | |
|---|---|---|---|---|---|---|
| Formulation | TMPEO (g) | DABCO 33-LV (mg) | Mondur MRS-2 (g) | TEGDME (g) | ΔT (° C.) | Gel time (min) |
| 1 | 4.0 | 7.8 | 1.0 | 3.0 | 13.6 | 11 |
| 2 | 10.0 | 63.3 | 2.5 | 7.5 | | 10 |
| 3 | 5.0 | 5.5 | 1.0 | | | 7 |
| 4 | 4.0 | 16.4 | 1.0 | 3.0 | 17.4 | 4.5 |
| 5 | 4.0 | 26.5 | 1.0 | 3.0 | 23.0 | 2.7 |
| 6 | 30.0 | 189.1 | 7.5 | 22.5 | 35.3 | 2.5 |

Note:
Tetraethylene glycol dimethyl ether (TEGDME) is a diluent

In one embodiment, the polymer fluid is a two-component system in which both fluids are aqueous and a hydrogel is formed by crosslinking of a polyol or hydroxyl-terminated polymer with divinyl sulfone (DVS). The addition of the DVS crosslinking agent at high pH allows for fast gelation (i.e., gel formation). The gelation time can be altered from minutes to hours by adjusting the pH and divinyl sulfone concentration. Non-limiting examples of such two-component systems are listed in Table II.

TABLE II

Two-component systems that use DVS as a cross-linker

| Formulation | 10 wt % PVA in H$_2$O (g) | DVS (mg) | 1M NaOH (mL) | Gel time (min) |
|---|---|---|---|---|
| 1 | 5.0 | 17.9 | 0.4 | 56 |
| 2 | 5.0 | 35.9 | 0.4 | 27 |
| 3 | 5.0 | 71.7 | 0.8 | 7 |
| 4 | 5.0 | 141.2 | 0.8 | 5 |
| 5 | 5.0 | 143.2 | 1.6 | 3.25 |

In another embodiment, the polymer fluid is a two-component system in which both fluids are aqueous and a hydrogel is formed by crosslinking of a polyol or hydroxyl-terminated polymer with glutaraldehyde (GA). Addition of the GA crosslinking agent at low pH allows for fast gelation. The gelation time can be altered from minutes to hours by adjusting the pH and GA concentration.

TABLE III

Examples of systems that use GA as a cross-linker.

| Formulation | 10 wt % PVA in H$_2$O (g) | GA 25 wt % soln in H$_2$O (mL) | 1M HCl (mL) | Gel time (min) |
|---|---|---|---|---|
| 1 | 5.0 | 0.2 | 0.2 | 75 |
| 2 | 5.0 | 0.4 | 0.2 | 60 |
| 3 | 5.0 | 0.2 | 0.6 | 6 |

In yet another embodiment, the polymer fluid is a two-component system in which both fluids are aqueous and a hydrogel is formed by crosslinking of an amine-terminated polymer with DVS. This reaction proceeds quickly at neutral pH, eliminating the need for pH modulation. The gel time can be altered from minutes to hours by adjusting the DVS concentration. Examples of amine-terminated polymers include polyethylenimine, polyallylamine, polylysine, and PAMAM dendrimers.

In yet another embodiment, the polymer fluid is a one-component system in which a polyurethane pre-polymer is subjected to a high concentration of tertiary amine catalyst to cause gelation. Gelation time can be altered from minutes to hours by adjusting the tertiary amine catalyst concentration. A variety of polyurethane pre-polymers may be formed by reacting any of the isocyanates listed above (in stoichiometric excess) with any of the polyols listed above. Examples of suitable amine catalysts include triethylenediamaine, triethanolamine, triethyleneamine, bis(2-dimethylaminoethyl) ether, 1-8-diazabicyclo[5.4.0]undec-7-ene, 1,1,3,3-tetramethylguanidine, and N,N-dimethylethanolamine.

In one embodiment, one component of the polymer fluid may contain a multifunctional molecule, polymer, or protein with available reactive functional groups, such as amine, thiol, hydroxyl, epoxy, or carboxylic acid. The other component of the polymer fluid may consist of a crosslinking molecule or polymer containing corresponding reactive groups, such as vinyl sulfone, epoxy, NHS-ester, isocyanate, isothiocyanate, maleimide, aldehyde, etc. Either component may also contain diluents, solvents, catalysts, surfactants, and/or radiopaque elements. In yet another embodiment, the first component could be the patient's own blood.

In another embodiment, one component of the polymer fluid contains a multifunctional molecule or polymer, preferably a polysaccharide such as alginate, gellan gum, or carrageenan, or modified derivative thereof. A second component of the fluid may contain the appropriate crosslinking ion, $Ca^{2+}$, $Na^+$, etc. in solution. Either component may further contain diluents, solvents, catalysts, surfactants, and/or radiopaque elements.

In another embodiment, the polymer fluid is a material that forms a gel at or near body temperature, such as agarose or methyl cellulose. Such a polymer fluid may include a composition of synthetic polymers with a lower critical solution temperature (LCST) behavior (i.e., materials that are miscible in all proportions below the LSCT but are immiscible above the LCST), such as poly(N-isopropylacrylamide). The polymer fluid may be a two-component system in which the second component modulates that temperature response of the first component (e.g., sodium chloride in the second component decreases the gel temperature of methyl cellulose in the first component). In another embodiment, either component may further contain diluents, solvents, catalysts, surfactants, and/or radiopaque elements.

In another embodiment, the polymer fluid is a two-component fluid in which one component contains a molecule or polymer which only forms a gel above or below a certain pH, while the other component contains the necessary acid or base to facilitate the phase change. For example, the two-component polymer fluid may include a first component comprising cross-linked poly acrylic acid (e.g., Carbopol) and NaOH as the second component. Either component may further contain diluents, solvents, catalysts, surfactants, and/or radiopaque elements.

In another embodiment, the polymer fluid may contain acrylate or other UV-polymerizable groups which may be activated in-situ by radiation from fluoroscopy or a related excitation source. By way of non-limiting example, any of the polyols listed herein may be modified by reaction with acryloyl chloride to create an acrylated pre-polymer that can be UV-cured.

In yet another embodiment, one component of the polymer fluid includes a silane-functionalized polymer or monomer, such as tetraethylorthosilicate, aminopropyl triethoxysilane, aminopropyl trimethoxysilane, silane-capped polyurethane pre-polymers, etc. The second component contains moieties which may cause silicate condensation by altering the pH such that hydrolysis of alkoxysilanes and subsequent silica condensation more favorable. Either component may further contain diluents, solvents, catalysts, surfactants, and/or radiopaque elements.

In yet another embodiment, the polymer fluids of the present invention may further comprise components exemplified by two or more of the embodiments described above. For example, one component may contain a polyamine and an alginate, while the second component may contain divinyl sulfone and calcium chloride. The presence of more than one distinct gel network may improve overall mechanical strength. Additionally, any of the embodiments outlined above may be further formulated to be radiopaque, fluorescent or otherwise visible by imaging techniques known to those skilled in the art. For example, radiopacity may be imparted by the incorporation of iodinated contrast materials, barium sulfate and/or metal particles such as tantalum or titanium, etc.

Table IV summarizes examples of four gelling systems outlined above, using the following abbreviations: polyvinyl alcohol (PVA); divinyl sulfone (DVS); trimethylolpropane ethoxylate (TMPEO); dibasic ether 3 (DBE-3); 80% Ethoxylated polyethyleneimine 35 wt % in H$_2$O (EPEI); polyurethane pre-polymer (Nanopol) (IP800); Dimethyl Sulfoxide (DMSO); and bis(2-dimethylaminoethyl)ether (ETS).

TABLE IV

Summary of the gelling systems outlined above.

| Example | Component 1 | Component 2 | Gel Time (min:sec) |
|---|---|---|---|
| 1 | 36.8 mg DABCO 33LV<br>4.01 g TMPEO (1014 Da) | 1.10 g Mondur MRS-2<br>2.99 g DBE-3 | 2:10 |

TABLE IV-continued

Summary of the gelling systems outlined above.

| Example | Component 1 | Component 2 | Gel Time (min:sec) |
|---|---|---|---|
| 2 | 5.04 g 10 wt % PVA (16 kDa) in $H_2O$ | 143.2 mg DVS 1600 µL 1M NaOH in $H_2O$ | 3:15 |
| 3 | 1.765 g 35 wt % EPEI (70 kDa) in $H_2O$ 1.78 g $H_2O$ | 42.5 mg DVS 1.50 g $H_2O$ | 2:20 |
| 4 | 1.20 g Nanopol IP800 1.24 g DMSO 0.125 g ETS | None | 1:30 |

Example 1 in Table IV represents an embodiment of a two-component polyurethane fluid in which the gel time can be adjusted from seconds to hours by altering the concentration of the catalyst (DABCO 33LV). The combination of components in Example 1 results in a fluid with a viscosity of 50 cP and a density of 1.11 g/ml. The compressive modulus of the resulting gel is 1.63 MPa. The measured internal temperature rise of a 30 g preparation of this formulation was 22.1° C.

Figure 4A:
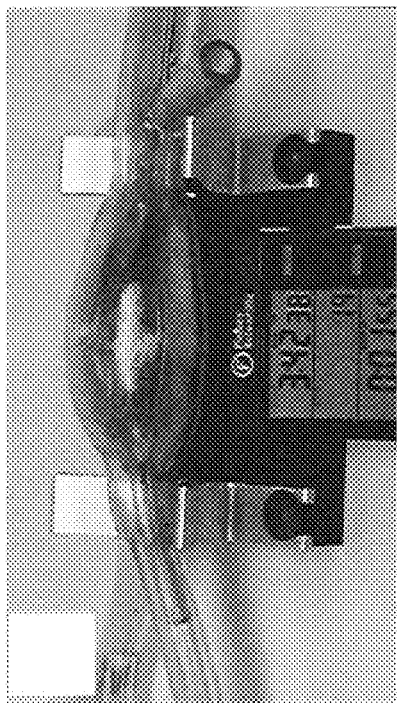
FIGS. 4A-D depict the filling of a polyurethane endobag (Endologix) within a silicone aneurysm model in accordance with one embodiment of the present invention.
Figure 4B:
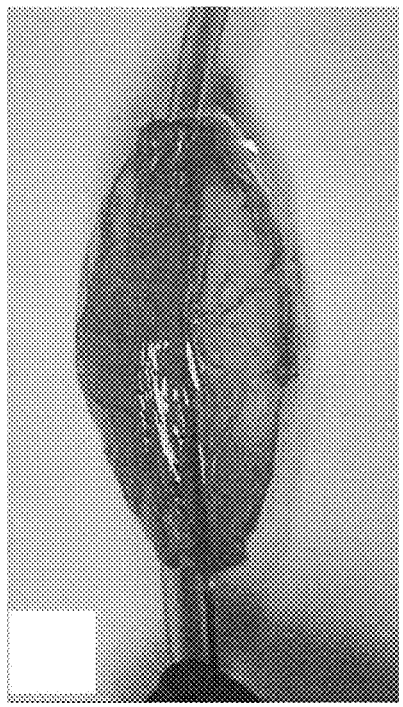
Figure 4C:
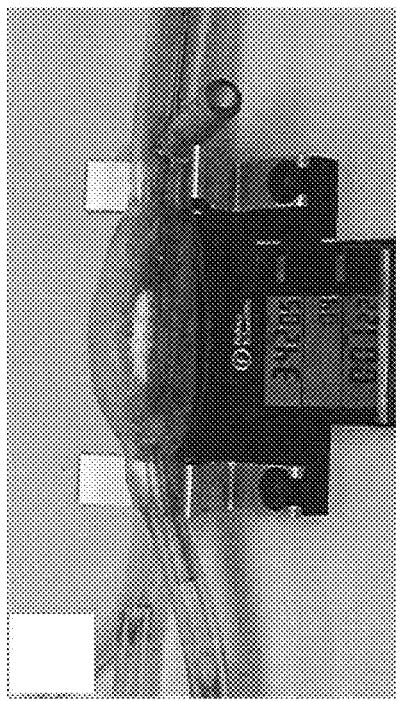
Figure 4D:
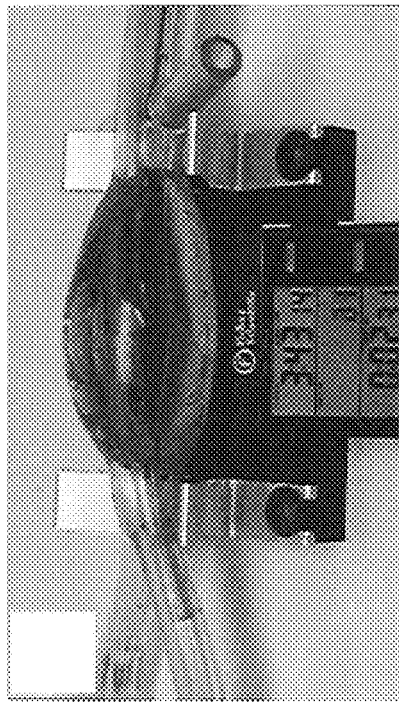

The gel from Example 1 was used in conjunction with an endobag (Endologix) as a component of an endovascular aneurysm repair system in which the endobag surrounds a stent placed in an abdominal aortic aneurysm (AAA). The endobag was filled with the two-component polymer fluid of Example 1 and allowed to conform to the irregular shape of an aneurysm model. Formation of the gel anchored the stent in place and excluded blood from the aneurysm. FIG. 4 illustrates the deployment of an in-situ forming gel 400 inside an endobag 410. Using a silicone aneurysm model 420 a length of tubing 130 was fitted through the center of a toroidal endobag 410 to simulate the presence of a stent. The endobag was flushed with polydimethylsiloxane (MW 2000) to remove as much air from the bag as possible and determine a suitable fill volume. Following the polydimethylsiloxane flush, 110 ml of the polyurethane gelling formula from Example 1 was injected into the endobag using a pneumatic gun at 70 psi of pressure. FIGS. 4A-4C depict the gradual filling of the endobag 110 with the two-component formulation of example 1. As shown in FIG. 1D, the endobag maintained the shape of the aneurysm due to the stability imparted by the gel.

Junctional Hemorrhage

Bleeding from external, non-compressible wounds located at interfaces between the extremities and the torso are often referred to as junctional hemorrhages. Sites at which junctional hemorrhage may occur include the groin/pelvic region (i.e., iliac and femoral bleeding), the axilla/clavicle region (i.e., brachial and subclavian arterial bleeding) and the neck (i.e., carotid bleeding). Junctional hemorrhages often occur in "non-compressible" areas, making it difficult to stop or limit bleeding from the wound. As used herein, a "wound", "wound surface," "wound area," or "wound bed" refers to any wound or injury located at or near an area of the body where an extremity such as the head, arm(s), or leg(s) meets the torso of the body.

Injuries leading to hemorrhage are often classified as resulting from either penetrating or blunt trauma. Penetrating trauma is characterized by the presence of a foreign object penetrating the skin leading to injury; gunshot wounds are one common example. Alternatively, blunt trauma is typically caused by a high force impact, resulting in internal trauma without a distinct open injury or wound track. As an example, pelvic fractures resulting from high force, motor vehicle crashes can lead to severe internal trauma and hemorrhage. The present invention allows the treatment of junctional hemorrhage arising from both penetrating and blunt injuries.

In one aspect, the present invention relates to systems and methods that utilize polymer fluids that form foams or gels to treat junctional hemorrhage. The polymer fluids can be delivered deep within a wound where they form in-situ foams or gels that conform to the shape of the wound. These foams or gels may stop or control bleeding by exerting pressure within the otherwise non-compressible wound. Moreover, the foams or gels can also reduce the available space for blood to pool within the wound, enhance coagulation and/or seal the surface of the wound. Unlike conventional hemostatic devices, these foams or gels are able to deeply penetrate the wound to form a continuous (e.g., monolithic) structure that extends to the surface of the wound such that compression forces at the surface can be transmitted to the entire area of the wound. Medical devices such as syringes or delivery catheters can be used to facilitate transport of polymer fluids to the wound area. In addition, such medical devices may be used to help retain the foam or gel within the wound area as described below.

For example, a flexible (i.e., compliant, semi-compliant or non-compliant) hemostatic structure with an opening at one end, such as bag or balloon, can be manually inserted into a wound. The polymer fluid can then be delivered into the open end of the bag and held in place by physical compression. In one embodiment, expansion of the in-situ forming foam forces the hemostatic bag to inflate, thereby pushing its outer surfaces further into the wound. The hemostatic bag may be porous so that at least a portion of the foam expands beyond the bag wall to contact and/or adhere to the wounded tissue. The number and distribution of such pores or slits can be arranged to optimize hemostasis and/or wound healing. For example, a plurality of pores may be located uniformly around the bag. In another example, a single pore within the portion of the bag that penetrates deepest into the wound may anchor the bag within the wound. In another example, a plurality of pores may be located uniformly around the bag.

Figure 5A:
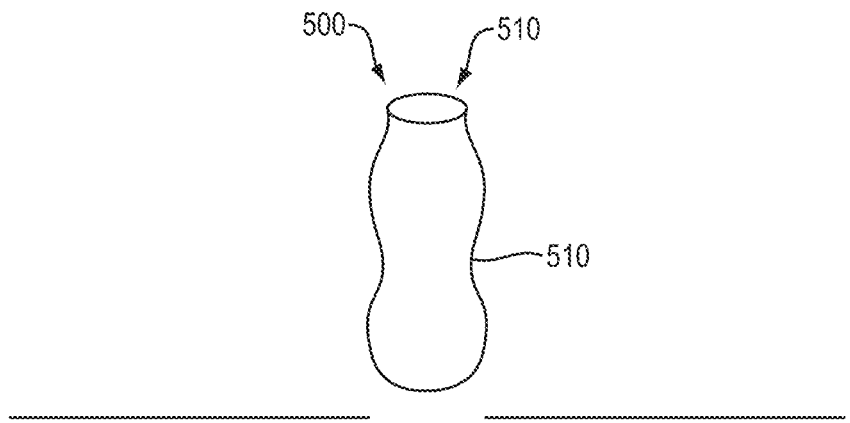
FIGS. 5A-B depict a balloon or bag for treating a junctional hemorrhage connected to a retrieval rope in accordance with one embodiment of the present invention.
Figure 5B:
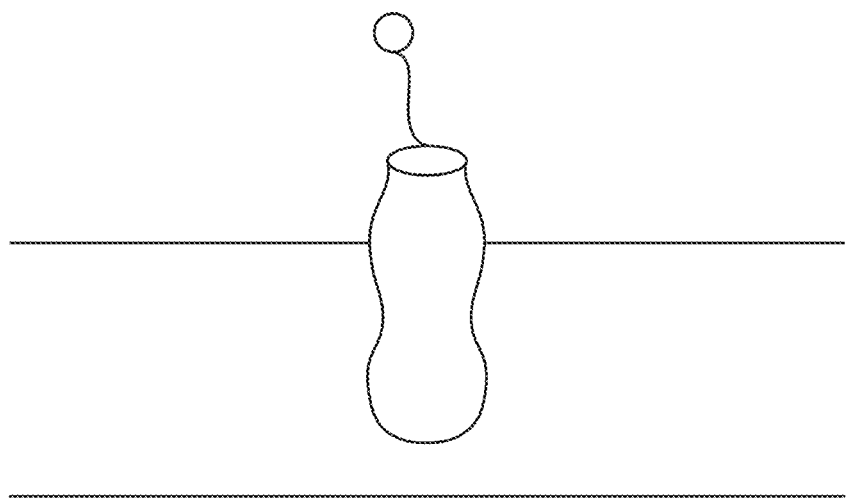

In one embodiment, the balloon or bag may comprise hemostatic agents such as gauze, sheets, powders, particles or related medical formulations (FIG. 5A). In one embodiment, the hemostatic agent may be biocompatible or bioresorbable. In another embodiment, the bag or balloon may include a means for retrieval from the wound, such as the retrieval rope depicted in FIG. 5B. The hemostatic bag may also include the bag-in-bag configuration described above.

Figure 6A:
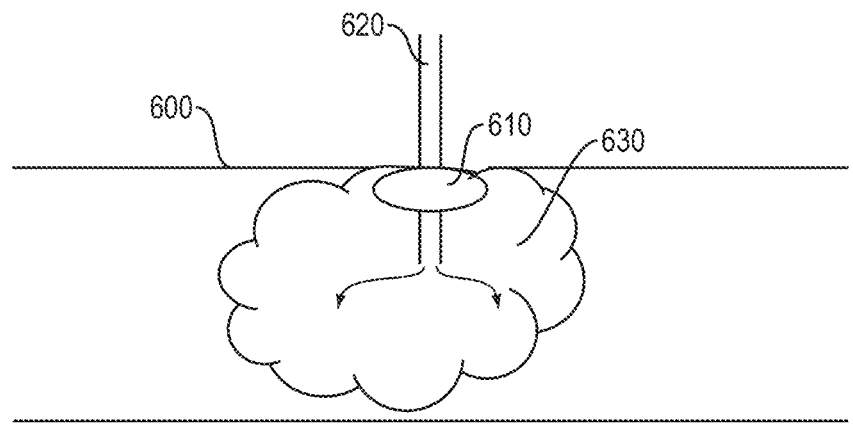
FIGS. 6A-B depict the use of a balloon or expandable pre-formed foam to seal the surface of a wound prior to delivery of a liquid foam formulation into the wound area, in accordance with one embodiment of the present invention.
Figure 6B:
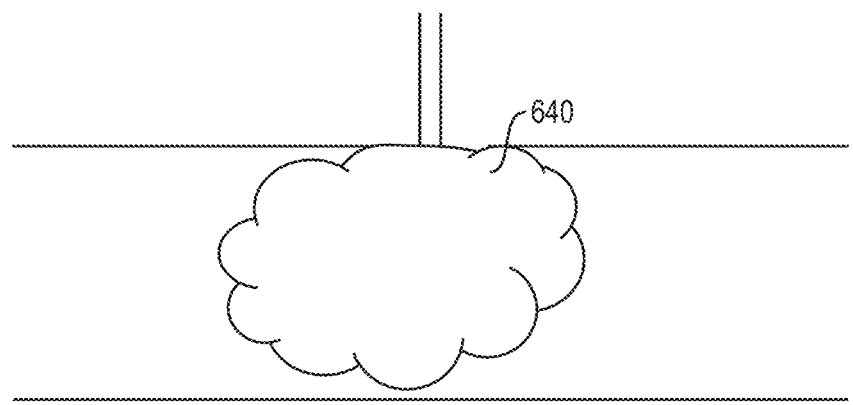

FIG. 6A provides another example, in which the wound surface 600 is sealed by the application of an inflatable balloon or expandable pre-formed foam 610. In one embodiment, the balloon or expandable pre-formed foam may include a shaft or passageway 620 through which a user may deliver liquid foam formulation into the wound area 630 after sealing of the wound surface by the balloon or expanded pre-formed foam 610. The foam formulation may then expand to fill the wound area 640, as shown in FIG. 6B. As described above, the balloon or foam may contain tissue adhesives/ligands or can be made porous to allow some liquid foam formulation to permeate through and contact the wound margins.

In one embodiment, the foams of the present invention may be used to drive a pre-formed, solid hemostatic material into the wound cavity to improve its depth of penetration and proximity to the source of bleeding. Examples of suitable hemostatic materials include, without limitation, glucosamine-based materials, cellulose, collagen, gelatin, fibrinogen, thrombin, fibrin, biologics, synthetic hemostatic peptides based on the RADA sequence, freeze-dried platelets, freeze-dried plasma, gelatin, silica particles, kaolin, glass beads, anti-fibrinolytic drugs and zeolites. Useful glucosamine-based materials include, without limitation, chitin, chitosan, and poly-N-acetyl glucosamine. Useful biologics include, without limitation, factor VII, factor XII, factor XI, factor VIII, factor IX or other coagulation factors from human or animal sources.

In one embodiment, the foam may include anti-fibrinolytic drugs such as, without limitation, tranexamic acid and aminocaproic acid. In another embodiment, the foam may include vasoconstrictors such as epinephrine, norepinephrine, amphetamines, vasopres sin, phenylephrine, pseudoephedrine, psilocybin and the like to induce constriction of major blood vessels. In yet another embodiment, the foam may include silver nitrate ($AgNO_3$), to promote clotting through a cautery, in addition to its antimicrobial activity. In yet another embodiment, pain relieving agents such as bupivacaine, lidocaine, ropivacaine, morphine or peptides may be incorporated into or onto the foam or bag. In yet another embodiment, disinfectants, antimicrobials, antibiotics or antifungals, such as iodine, iodine precursors or silver ions, may be incorporated into or onto the foam or bag. The agents listed above may be combined on one device to provide multi-functionality and may be formulated to provide a controlled or sustained release (e.g., polymer coatings, polymer fibers, core-sheath fibers and microspheres).

In another embodiment, the foams or gels of the present invention may be deployed adjacent or near to injuries (e.g., in treatment of blunt injuries). As a non-limiting example, blunt trauma to the pelvis often results in displacement of the pelvic ring. Hemorrhage resulting from these injuries is often severe and can be diffuse due to in bleeding from the venous plexuses. This bleeding typically occurs into the retroperitoneal space, and as a closed space, this bleeding has the ability to naturally tamponade. However, displacement of the pelvic ring commonly leads to injury of the retroperitoneal space that disrupts this closed space, resulting in bleeding that can lead to exsanguination. In one embodiment, the present invention allows this "non-compressible" hemorrhage to be compressed over a wide surface area by applying the in-situ foam or gel near or adjacent to the injury. For example, the in-situ foam or gel may be delivered into the retroperitoneal space, thereby applying pressure over a large surface area to provide better conformal contact and compression of bleeding surfaces than pre-formed laparotomy pads. Alternatively, the in-situ foam or gel may be applied in the pre-peritoneal space (the space adjacent to the injury) such that the space is pressurized leading to compression of the injured site.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention. In cases where the present specification and a document incorporated by reference include conflicting and/or inconsistent disclosure, the present specification shall control. If two or more documents incorporated by reference include conflicting and/or inconsistent disclosure with respect to each other, then the document having the later effective date shall control.

The indefinite articles "a" and "an," as used herein in the specification and in the claims, unless clearly indicated to the contrary, should be understood to mean "at least one." The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc. As used herein, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items.

We claim:

1. A method of treating a patient, comprising:
   providing a structure comprising a first and second bag, wherein said second bag at least partially covers said first bag, the first and second bags being attached to each other,
   inserting said structure into a cavity within the patient, inserting a polymer into said first bag after said structure is inserted into said cavity, and forming a foam from said polymer after said polymer is inserted into said first bag.

2. The method of claim 1, wherein said method is used to treat an intestinal hemorrhage.

3. The method of claim 1, wherein said method is used to treat a junctional hemorrhage.

4. The method of claim 1, wherein said method is used to treat a sinus hemorrhage.

5. The method of claim 1, wherein said foam expands within said structure to exert pressure on a wall of said cavity.

6. The method of claim 1, wherein said first and second bags each comprise a plurality of pores.

7. The method of claim 6, wherein at least of portion of said foam extends through at least some of the pores of said first and second bags.

8. The method of claim 1, wherein said foam comprises a compound that promotes blood clotting.

9. The method of claim 1, further comprising the step of removing said structure from the patient by applying tension to the first bag.

10. The method of claim 1, wherein said polymer comprises polyurethane.

11. The method of claim 10, wherein said polymer further comprises an isocyanate compound selected from the group consisting of hexamethylene diisocyanate, toluene diisocyanate, methylene diphenyl diisocyanate, and isophorone diisocyanate.

12. The method of claim 11, further comprising a hydroxyl-functionalized polymer.

13. The method of claim 1, further comprising the step of introducing a gas into at least one of said first bag and said second bag after said step of forming said form.

14. The method of claim 1, wherein at least one of said first bag and said second bag comprises multiple sections that are retained in proximity to one another using an attachment means.

15. The method of claim 1, wherein said first and second bags are attached to one another at a distal end of each of said first and second bags.

16. A method of treating a hemorrhage, comprising:

providing a structure comprising a first and second bag, said first bag comprising a plurality of pre-formed foam components, wherein said second bag at least partially covers said first bag, the first and second bags being attached to each other, and inserting said structure at the site of a hemorrhage.

17. The method of claim 16, wherein said hemorrhage is an intestinal hemorrhage.

18. The method of claim 16, wherein said hemorrhage is a junctional hemorrhage.

19. The method of claim 16, wherein said hemorrhage is within an organ.

20. The method of claim 16, further comprising the step of removing said structure from said patient by applying tension to said first bag.

21. The method of claim 16, wherein said pre-formed foam components are attached end-to-end.

\* \* \* \* \*